United States Patent
Boyle, Jr. et al.

(10) Patent No.: US 6,175,024 B1
(45) Date of Patent: Jan. 16, 2001

(54) SYNTHESIS OF FUNCTIONALIZED ESTERS

(75) Inventors: William J. Boyle, Jr., Somerset County; Indira Reddy, Morris County; Zhenrong Qian, Morris County; Heng Eric Su, Morris County, all of NJ (US); David Ryckman, Seattle, WA (US)

(73) Assignee: AlliedSignal Inc., Morristown, NJ (US)

( * ) Notice: Under 35 U.S.C. 154(b), the term of this patent shall be extended for 0 days.

(21) Appl. No.: 09/261,519

(22) Filed: Mar. 3, 1999

(51) Int. Cl.$^7$ .............................. C07B 33/00; C07C 69/66
(52) U.S. Cl. .......................... 554/133; 554/225; 560/179; 560/226; 562/579; 562/602
(58) Field of Search ..................... 560/179, 226; 562/579, 602; 554/133, 225

(56) References Cited

PUBLICATIONS

Chemical Abstracts, vol. 55, No. 6, Mar. 20, 1961 Columbus, Ohio, US; abstract No. 5333I, D.G.M. Diaper et al.: "An Improved preparation of omega–hydroxy aliphatic acids and their esters" p. 1961; column 1; XP002140424 abstract & Canadian Journal of Chemistry., vol. 38, 1960, pp. 1976–1982, National Research Council. Ottawa., CA ISSN: 0008–4042.

Armin Guffisberg et al.: "Synthese des (+–)–Oncinotins" Helvetica Chimica Acta., vol. 57, No. 2 Mar. 13, 1974, pp. 434–440, XP002140423 Verlag Helvetica Chimica Acta. Basel., CH ISSN: 0018–019X p. 437, paragraph 4–p. 438, paragraph 1.

*Primary Examiner*—Paul J. Killos
(74) *Attorney, Agent, or Firm*—Colleen D. Szuch; Maria C. Walsh

(57) ABSTRACT

A method of preparing an ester of a carboxylic acid functionalized with a moiety selected from the group consisting of halides, sulfonates, ethers, hydroxyl, amines, and aldehydes, said method comprising: (a) providing either a carboxylic acid having a vinyl group or an ester thereof; (b) functionalizing the vinyl carbon closest to the carboxyl group with said moiety, wherein said functionalizing comprises cleaving said vinyl group.

22 Claims, No Drawings

SYNTHESIS OF FUNCTIONALIZED ESTERS

FIELD OF INVENTION

The present invention relates to the synthesis of functionalized esters. More specifically, this invention relates to the synthesis of ethyl 10-bromodecanoate.

BACKGROUND OF THE INVENTION

Functionalized esters, such as ethyl 10-bromodecanoate, are used commonly in the synthesis of fine organic chemicals which, in turn, are used in pharmaceutical, flavor and fragrance, and agricultural products just to name a few. These compounds are especially useful as intermediates since the relatively-high reactivity of their functional group facilitates the compound's combination with other compounds to form complex esters. For example, ethyl 10-bromodecanoate is used as an intermediate in the production of drug carriers in the pharmaceutical field.

The traditional preparation of such functionalized esters, however, involves the consumption of expensive raw materials in reactions which are complex and difficult to control. Additionally, these reactions tend to have low yields and to result in the generation of unwanted by-products. For example, the conventional synthesis of ethyl 10-bromodecanoate involves a three-step process which is complex, costly and inefficient.

In the first step, 1,8-dibromooctane is alkylated using diethylmalonate, sodium ethoxide and ethanol to form 8-bromo octylmalonic acid diethylester. Besides being a relatively expensive, synthesized material, 1,8-dibromo octane is terminated in similar bromine functionality, which are equally as likely to react. Consequently, reactions involving just one of the bromine groups, like the alkylation reaction described above, tend to be difficult to control and result in poor selectivities. To some extent, the reaction of both bromo groups is unavoidable and the resulting compound, octanebismalonic acid tetraethylester, is similar enough to 8-bromo octylmalonic acid diethylester that separation between the two is difficult, thereby resulting in poor yields. Furthermore, the difficult separation of these compounds is particularly problematic since pharmaceutical applications mandate extremely high purity levels.

In the second step, 10-bromodecanoic acid is produced through the decarboxylation of the distilled 8-bromo octyl-malonic acid diethylester produced in the first step. The timing of the termination of the decarboxylation is very critical, otherwise over-decarboxylation will occur to give low yields and impurities. Additionally, this step produces hazardous ethyl bromide as a byproduct which necessitates special handling.

In the third step, the desired product, ethyl 10-bromodecanoate, is produced through the esterification of 10-bromodecanoic acid in ethanol. The overall yield of this process is about 47%. In general, this process is costly, complex, inefficient, and produces hazardous waste.

Accordingly, there is a need for a process for preparing functionalized esters that uses relatively inexpensive starting materials and that involves reactions which are controlled readily to produce the desired product at high yields with minimal formation of hazardous byproducts. The present invention fulfills this need among others.

DESCRIPTION OF THE INVENTION AND PREFERRED EMBODIMENTS

The present invention overcomes the problems encountered in the conventional preparation of functionalized esters by using a commercially-available or readily-synthesized starting material having a vinyl group and a carboxyl group. The vinyl group facilitates convenient functionalization of the compound while the carboxyl group is readily esterified. Since the vinyl and carboxyl moiety of the starting material are significantly different and can be reacted selectively, high yields of the functionalized esters can be achieved with a minimal production of by-products including hazardous materials. Additionally, by starting with a material having a carbon backbone longer than that of the desired product, low-selectivity alkylation reactions for increasing molecule length can be avoided.

One aspect of the invention is a method of preparing a functionalized ester using a starting material having a vinyl group and a carboxyl group. In a preferred embodiment, the process comprises: (a) providing a carboxylic acid having a vinyl group; and (b) functionalizing the vinyl carbon closest to the carboxyl group with a moiety selected from the group consisting of halides, sulfonates, ethers, hydroxyl, amines, and aldehydes and their derivatives, wherein the step of functionalizing comprises cleaving the vinyl group.

As mentioned above, the vinyl and carboxyl groups of the starting material facilitate its functionalization and esterification respectively. During functionalization, the double bond of the vinyl group is cleaved and the functionality is introduced. It is well known that the vinyl group may be cleaved with high selectivity since double bonds tend to be reactive sites in a molecule. Approaches to cleaving a vinyl group are known in the art, and include, for example, ozonization, oxidation using osmium oxide, and oxidation using potassium permanganate. Furthermore, it is well known that the step of cleaving the vinyl group can be performed in a single step or a number of discrete steps.

Preferably, cleaving comprises ozonolysis of the vinyl group to form an ozonide and then reduction of the ozonide in such a way as to avoid or minimize formation of an acid. In the preferred embodiment, the work up of the ozonolysis is such that the ozonide is reduced to a hydroxylated compound. For example, the ozonization and reduction of 10-undecylenic acid may be conducted according to the following reaction:

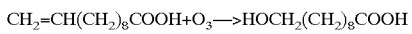

$$CH_2=CH(CH_2)_8COOH + O_3 \rightarrow HOCH_2(CH_2)_8COOH$$

Reduction can be effected, for example, using a basic solution of sodium borohydride ($NaBH_4$). It should be noted, however, that other conventional techniques for reducing the ozonide are known. For example, the ozonide may be reduced to an aldehyde ($OCH_3(CH_2)_8COOH$) and then to $NH_2CH_2(CH_2)_8COOH$ through reduction amination. It is difficult, however, to avoid the production of acids in this latter process. Ozonolysis and reduction may be performed in two or more separate reactions, although, preferably, the ozonide is reduced immediately without removal from the reaction mixture since it tends to be explosive.

After cleaving, it may be desirable to introduce particular functionality into the compound by converting the terminal group which may be, for example, a hydroxyl or an amine group. Conversion reactions are well known and depend upon the terminal group of the cleaved intermediate and the desired functionality. For example, in the conversion of the hydroxyl group to bromine, it is known to react the hydroxylated compound with $PBr_3$ in acetic acid. In this case, however, it has been found that these complex reagents are not necessary and the conversion can be effected through contact with a hydrogen bromide solution. For example, the conversion of 10-hydroxydecanoic acid may be conducted according to the following reaction:

$$HOCH_2(CH_2)_8COOH + HBr \longrightarrow BrCH_2(CH_2)_8COOH + H_2O$$

In esterifying the carboxyl group, an alcohol, ROH, reacts with the carboxyl group to form water and an ester of the alkyl group of the alcohol. The particular choice of alcohol depends upon the desired alkyl group to be esterified to the compound. Esterification is a well known process and those skilled in the art can determine readily the conditions under which to conduct the reaction. For example, 10-bromodecanoic acid may be esterified according to the following reaction:

$$BrCH_2(CH_2)_8COOH + CH_3CH_2OH \longrightarrow BrCH_2(CH_2)C(O)OCH_3CH_2 + H_2O.$$

The order of functionalization and esterification is not critical. For example, rather than performing an ozonolysis of the starting material, for example, 10-undecylenic acid, as described above, the starting material first may be esterified with ethanol or other alcohol to form an ester, for example, ethyl 10-undecylenate. Next, the ester can undergo functionalization by first ozonating the ester and then reducing the ozonide using, for example, sodium borohydride to form a hydroxylated ester, for example, ethyl 10-hydroxydecanoate. The hydroxylated ester finally is converted to the desired functionalized ester using, for example, $PBr_3$ to form ethyl 10-bromodecanoate.

Although not critical, functionalization prior to esterification usually results in higher yields. Functionalization prior to esterification also is more convenient since highly-effective solutions for converting the hydroxyl group to a bromo group, such as aqueous HBr, will not work once the carboxylic acid is esterified since HBr will convert the ester back to an acid. Therefore, it is generally preferred that functionalization precede esterification.

Once functionalized and esterified, the product may be recovered using known techniques such as distillation, filtration and/or reaction.

The synthesis method of the present invention is particularly effective in preparing functionalized esters having the formula:

$$XCH_2(CR_1R_2)_n\bullet COOR \quad (1)$$

from a starting material having the formula:

$$R_3R_4C=CH(CR_1R_2)_n\bullet COOH \quad (2)$$

wherein:
X is the moiety selected from the group consisting of halides, sulfonates, ethers, hydroxyl, amines, and aldehydes and their derivatives;
each of $R_1$, $R_2$, $R_3$, and $R_4$ is independently selected from hydrogen, an unsubstituted or substituted aliphatic radical, or unsubstituted or substituted aromatic radical;
R is selected from an unsubstituted or substituted aliphatic radical, or unsubstituted or substituted aromatic radical; and
n is an integer from 2 to 20.

In Formulas (1) and (2), each of $R_1$, $R_2$, $R_3$, and $R_4$ preferably is selected from hydrogen, an unsubstituted or substituted $C_1$–$C_{10}$ aliphatic radical, an unsubstituted or substituted $C_3$–$C_{10}$ alicyclic radical, or an unsubstituted or substituted $C_6$–$C_{15}$ aromatic radical. More preferably, each of $R_1$, $R_2$, $R_3$, and $R_4$ is independently selected from an unsubstituted or substituted $C_1$–$C_{10}$ alkyl, an unsubstituted or substituted $C_3$–$C_8$ cycloalkyl, an unsubstituted or substituted 3–6 ring member heterocyclic radical, an unsubstituted or substituted $C_6$–$C_{15}$ aryl, or an unsubstituted or substituted $C_7$–$C_{11}$ aralkyl. Examples of substitution groups include fluorine, $C_1$–$C_6$ alkyls, $C_1$–$C_6$ halogenated alkyls, $C_6$–$C_{15}$ aryls, $C_1$–$C_6$ alkoxys, nitros, aminos (primary and secondary), amidos, and cyanos.

As a $C_1$–$C_{10}$ alkyl, each of $R_1$, $R_2$, $R_3$, and $R_4$ may be a straight chain or branched molecule, for example, methyl, ethyl, n-propyl, isopropyl, n-butyl, isobutyl, tert-butyl, n-pentyl, neopentyl, n-hexyl, n-heptyl, n-octyl, or 2-ethylhexyl. Additionally, any of these groups may substituted with methoxy, ethoxy, n-propoxy, isopropoxy, n-butoxy, methanesulphonyl, cyano, bromine, chlorine or fluorine, among others, to form such substituted alkyl groups as methoxymethyl, 2-methoxyethyl, 2-ethoxymethyl, 2-n-butoxyethyl, 3-methoxypropyl, 1-methoxybutyl, 2-methoxybutyl, methanesulphonylmethyl, 2-methanesulphonylethyl, 2-cyanoethyl, 2-fluoroethyl, 2,2,2-trifluoroethyl, trichloromethyl, 2-chloroethyl, 2-(chloromethyl)ethyl, 2,2,2-trichloroethyl, 2-chloro-n-propyl or 3-chloro-n-butyl. In a preferred class of alkyls, each of $R_1$, $R_2$, $R_3$, and $R_4$ is an $C_1$–$C_6$ alkyl, which may be substituted by cyano, halogen or $C_1$–$C_4$ alkoxy, especially methyl, ethyl, n-butyl, 2-cyanoethyl, 1-(chloromethyl) ethyl or 2-methoxyethyl. In another preferred class of alkyls, each of $R_1$, $R_2$, $R_3$, and $R_4$ is branched alkyl, preferably a $C_2$–$C_6$ branched alkyl, especially isobutyl.

As a $C_3$–$C_8$ cycloalkyl, each of $R_1$, $R_2$, $R_3$, and $R_4$ may be, for example, cyclopropyl, cyclobutyl, cyclopentyl, methylcyclopentyl, cyclohexyl, methylcyclohexyl, dimethylcyclohexyl, cycloheptyl or cyclooctyl, preferably cyclohexyl. Any of these groups may be substituted with, for example, methoxy, ethoxy, n-propoxy, isopropoxy, n-butoxy, cyano, chlorine or fluorine. In a preferred class of cycloalkyl, each of $R_1$, $R_2$, $R_3$, and $R_4$ is a $C_5$–$C_7$ cycloalkyl, and, more preferably, cyclohexyl.

As a 3–6 member heterocyclic radical, each of $R_1$, $R_2$, $R_3$, and $R_4$ may include any known heterocyclic atom such as N, O, and S. Suitable heterocycles include, for example, pyridine, pyran, thiophan, pyrrole, furan, and thiophen.

As a $C_6$–$C_{15}$ aryl, each of $R_1$, $R_2$, $R_3$, and $R_4$ may be, for example, phenyl, o-tolyl, m-tolyl, p-tolyl, o-xylyl, m-xylyl, p-xylyl, alpha-naphthyl or beta-naphthyl. Any of these groups may be substituted with, for example, halogen, $C_1$–$C_4$ alkoxy or nitro. In a preferred class of aryls, each of $R_1$, $R_2$, $R_3$, and $R_4$ is $C_6$–$C_8$ aryl or $C_{12}$–$C_{14}$ aryl, and, more preferably, phenyl or naphthyl.

As $C_7$–$C_{13}$ aralkyl, each of $R_1$, $R_2$, $R_3$, and $R_4$ may be, for example, benzyl, 4-methylbenzyl, o-methoxybenzyl, p-methoxybenzyl, diphenylmethyl, 2-phenylethyl, 2-phenylpropyl or 3-phenylpropyl, preferably $C_7$–$C_9$ aralkyl, especially benzyl.

In an even more preferred embodiment, each of $R_1$, $R_2$, $R_3$, and $R_4$ is hydrogen, thereby simplifying Formulas (1) and (2) to formulas (3) and (4), respectively, below:

$$XCH_2(CH_2)_n\bullet COOR \quad (3)$$

$$CH_2=CH(CH_2)_n\bullet COOH \quad (4)$$

In the preferred and more preferred embodiments, R is the same for $R_1$, $R_2$, $R_3$, and $R_4$ above except that R cannot be hydrogen. In an even more preferred embodiment, R is a $C_1$–$C_3$ alkyl group, and, most preferably, it is an ethyl group.

The moiety, X, preferably is a halide or an aromatic sulfonate prepared from a sulfonic acid, such as, for example, para-toluenesulfonic acid (tosylate), methanesulfonic acid and bromobenzenesulfonic acid. More preferably, it is a halide selected from chlorine, bromine, or iodine, or an aromatic sulfonate. Most preferably, it is bromine.

The integer, n, preferably is from 4 to 12, and, more preferably, from 8 to 10. Most preferably, n is 8. It is noteworthy to mention that if n is greater than 1, thereby resulting in a plurality of $R_1$ and $R_2$ groups, each $R_1$ and $R_2$ is independently selected such that, for example, one $R_1$ may differ from another within the same molecule.

In the most preferred embodiment, the functionalized ester is ethyl 10-bromodecanoate, wherein $R_1$ and $R_2$ are hydrogen, X is bromine, R is ethyl, and n is 8, and the starting material is 10-undecylenic acid, which is commercially available and readily derived from naturally-occurring oils such as castor oil.

According to the present invention, a functionalized ester can be synthesized with high yields. For example, in the preparation of ethyl 10-bromodecanoate, the yield is preferably no less than 50% and, more preferably, no less than about 60%.

The following example is illustrative of the practice of the present invention.

EXAMPLE 1

This example illustrates the synthesis of ethyl 10-bromodecanoate from 10-undecylenic acid where the functionalization is performed prior to the esterification.

The functionalization first involved the ozonization and reduction of the 10-undecylenic acid according to the following reaction:

  (Step I)

The reactor used was a 2 L vessel equipped with a cooling jacket filled with ethylene glycol and water, a mechanical agitator, a thermocouple, a gas sparger, and a cooled condenser. The gas sparger was operatively connected to an ozone generator and a source of air and nitrogen.

To the reactor was added 186.14 g (1 mol) of 99% pure 10-undecylenic acid (commercial source) in 475 g absolute ethanol. The mixture was cooled to −5° C. The reaction mixture was sparged first with air to agitate it, and then with ozone at a rate of about 0.75 lb/day. After about four hours, the reaction mixture was checked periodically (every hour or so) for the presence of olefin. Once the olefin was consumed, the reaction mixture was sparged with nitrogen for half an hour to sparge the residual ozone while still cooling. The reaction mixture (670 g) containing the ozonide was drained into a stoppered flask and kept cool with dry ice.

The reaction mixture containing the ozonide next was reduced by adding it dropwise to a 5 L reactor containing 112 g (1.4 mol) of 50% NaOH and 54.05 g (1.4 mol) of 98% pure $NaBH_4$ dissolved in 550 g absolute ethanol. The reaction mixture in the 5 L reactor was stirred mechanically and maintained at about 0–5° C. with dry ice. After all the ozonide was reduced, the mixture was stirred for 8 h at room temperature such that the solvent was evaporated leaving 624 g of 10-hydroxydecanoic acid sodium salt (white solid).

The 10-hydroxydecanoic acid sodium salt then was dissolved in 2200 g of water and placed in the 5 L reactor. The reactor was equipped with an addition funnel. Through the funnel, 1095 g (3.0 mol) of 10% HCl solution was added dropwise to the reactor while stirring and cooling to maintain the temperature below 25° C. The reaction mixture was stirred for about 4–6 h. During this time, hydrogen was liberated and a white solid formed. The solids were washed repeatedly with water, filtered, and then dried under nitrogen. The residue was 92.24% pure 10-hydroxydecanoic acid. The yield was 90%.

Functionalization next involved the introduction of bromine functionality into the 10-hydroxydecanoic acid according to the following reaction:

  (Step II)

Specifically, 153.05 g of 10-hydroxydecanoic acid was mixed with 758.53 g of 48% HBr and heated to 125–130° C. for about 9 h with vigorous stirring. The reaction mixture phase separated at about 50° C. The top organic phase was 180.5 g 10-bromodecanoic acid and a trace amount of HBr which acted as a catalyst for esterification in the next step. The bottom phase comprised HBr and could have been recycled.

After functionalization, 10-bromodecanoic acid was then esterified according to the following reaction:

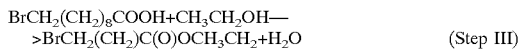  (Step III)

To this end, the 180.5 g of 10-bromodecanoic acid from Step II was added to the 1l reactor (described above) along with 645 g of absolute ethanol. The mixture was heated and stirred for about 3.5 h. GC analysis confirmed that reaction was completed when 10-bromodecanoic acid could not be detected. Next, excess ethanol and residual water were removed through evaporation leaving 197.8 g of 94.9% pure ethyl 10-bromodecanoate residue. 150 g MTBE was added to the ethyl 10-bromodecanoate residue which then was washed repeatedly with 10% sodium carbonate solution followed by water. The mixture was phase separated to obtain 340.7 g of a mixture of ethyl 10-bromodecanoate and MTBE. According to GC analysis the yield from Steps II and III was 89.7%.

Finally, the ethyl 10-bromodecanoate was purified through distillation using a 15-tray Older Shaw column equipped with a cold water-cooled condenser, a thermocouple, a heating mantle, a stirrer and a 500 ml 3-neck round-bottomed flask vacuum system capable of pulling a vacuum of 5 mm Hg. The 340.7 g of the mixture of ethyl 10-bromodecanoate and MTBE mixture from Step III was placed in the 500 ml round-bottomed flask. A main cut was collected at a pot temperature of 180–275° C., a head temperature of 121–123° C., and a reflux ratio of 1/5. The main cut had a composition of 99% pure ethyl 10-bromodecanoate and the distillation yield was 69.2%.

What is claimed is:

1. A method of preparing an ester of a carboxylic acid functionalized with a moiety selected from the group consisting of halides, sulfonates, ethers, hydroxyl, amines, and aldehydes and derivatives thereof, comprising:

functionalizing either a carboxylic acid having a vinyl group or an ester of said carboxylic acid such that the vinyl carbon closest to the carboxyl group is functionalized with said moiety, wherein said functionalizing comprises cleaving said vinyl group, wherein cleaving comprises ozonolysis of said vinyl group to form an ozonide.

2. The method of claim 1, wherein said cleaving comprises:

reduction of said ozonide to form a hydroxyl group on said vinyl carbon closest to the carboxyl group.

3. The method of claim 2, wherein functionalizing further comprises:

reacting said hydroxyl group with said moiety if said moiety is other than hydroxyl.

4. The method of claim 1, further comprising:
esterifying said carboxylic acid using an alcohol.

5. The method of claim 4, wherein said functionalizing is performed before said esterifying.

6. The method of claim 4, wherein said esterifying is performed before said functionalizing.

7. The method of claim 1, wherein said functionalizing comprises:
ozonating said vinyl group to form an ozonide;
reducing said ozonide to form a hydroxycarboxylic acid; and
converting said hydroxycarboxylic acid to a bromo carboxylic acid.

8. The method of claim 7, wherein said ozonide is reduced with sodium borohydride.

9. The method of claim 7, wherein hydroxycarboxylic acid is converted to said bromo carboxylic acid using aqueous HBr.

10. The method of claim 7, wherein said esterifying of said carboxylic acid comprises reacting said carboxyl group with ethanol.

11. A method of preparing a functionalized ester having the formula:

$$XCH(CR_1R_2)_n\bullet COOR$$

wherein:
n is an integer from 2 to 20;
X is a moiety selected from the group consisting of halides, sulfonates, ethers, hydroxyl, amines, and aldehydes and derivatives thereof; and
R is selected from an unsubstituted or substituted aliphatic radical, or unsubstituted or substituted aromatic radical; and
each of $R_1$ and $R_4$ is independently selected from hydrogen, an unsubstituted or substituted aliphatic radical, or unsubstituted or substituted aromatic radical, said method comprising:
functionalizing either said starting material or an ester of said starting material such that the vinyl carbon closest to the carboxyl group is functionalized with said moiety, wherein said functionalizing comprises cleaving said vinyl group wherein cleaving comprises ozonolysis of said vinyl group to form an ozonide.

12. The method of claim 11, wherein each of $R_1$, $R_2$, $R_3$, and $R_4$ is independently selected from hydrogen, an unsubstituted or substituted $C_1$–$C_{10}$ aliphatic radical, an unsubstituted or substituted $C_3$–$C_{10}$ alicyclic radical, or an unsubstituted or substituted $C_6$–$C_{15}$ aromatic radical, and wherein R is selected from an unsubstituted or substituted $C_1$–$C_{10}$ aliphatic radical, an unsubstituted or substituted $C_3$–$C_{10}$ alicyclic radical, or an unsubstituted or substituted $C_6$–$C_{15}$ aromatic radical.

13. The method of claim 12, wherein each of $R_1$, $R_2$, $R_3$, and $R_4$ is independently selected from hydrogen, an unsubstituted or substituted $C_1$–$C_6$ alkyl, an unsubstituted or substituted $C_5$–$C_7$ cycloalkyl, an unsubstituted or substituted $C_6$–$C_8$ aryl, or an unsubstituted or substituted $C_7$–$C_9$ aralkyl.

14. The method of claim 13, wherein each of $R_1$, $R_2$, $R_3$, and $R_4$ is hydrogen.

15. The method of claim 14, wherein n is an integer from 6 to 10, X is a halide or sulfonate, and R is a $C_1$–$C_3$ alkyl.

16. The method of claim 15, wherein X is a halide selected from the group consisting of chlorine, bromine, and iodine, or an aromatic sulfonate.

17. The method of claim 16, wherein said X is bromine or an aromatic sulfonate.

18. The method of claim 17, wherein n is 8, X is bromine, and R is an ethyl group.

19. A method of preparing ethyl 10-bromodecanoate comprising:
ozonating 10-undecylenic acid to form an ozonide;
reducing said ozonide using sodium borohydride to form 10-hydroxydecanoic acid;
reacting said 10-hydroxydecanoic acid with aqueous hydrogen bromide to form 10-bromodecanoic acid; and
reacting said 10-bromodecanoic acid with ethanol to form ethyl 10-bromodecanoate.

20. The method of claim 19, wherein said yield of 99% pure ethyl 10-bromodecanoate is no less than 50%.

21. The method of claim 20, wherein said yield of 99% pure ethyl 10-bromodecanoate is no less than 60%.

22. The method of claim 20, further comprising purifying said ethyl 10-bromodecanoate using distillation.

* * * * *